United States Patent
Zhu et al.

(10) Patent No.: US 7,769,437 B2
(45) Date of Patent: Aug. 3, 2010

(54) METHOD AND APPARATUS FOR DETERMINING CHANGES IN HEART FAILURE STATUS

(75) Inventors: Qingsheng Zhu, Little Canada, MN (US); Julio C. Spinelli, Shoreview, MN (US); Bruce H. KenKnight, Maple Grove, MN (US); Jay A. Warren, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1172 days.

(21) Appl. No.: 11/299,876

(22) Filed: Dec. 12, 2005

(65) Prior Publication Data

US 2006/0089679 A1 Apr. 27, 2006

Related U.S. Application Data

(63) Continuation of application No. 10/001,223, filed on Nov. 15, 2001, now Pat. No. 6,980,851.

(51) Int. Cl.
*A61B 5/04* (2006.01)

(52) U.S. Cl. .................. 600/513; 600/516; 600/517; 600/521; 607/18

(58) Field of Classification Search .............. 607/32, 607/1–9; 600/515–519
See application file for complete search history.

(56) References Cited

U.S. PATENT DOCUMENTS

| | | | |
|---|---|---|---|
| 4,899,758 A | 2/1990 | Finkelstein et al. | |
| 5,201,321 A * | 4/1993 | Fulton | 600/515 |
| 5,307,263 A | 4/1994 | Brown | |
| 5,311,874 A * | 5/1994 | Baumann et al. | 600/518 |
| 5,330,505 A * | 7/1994 | Cohen | 607/6 |
| 5,334,222 A | 8/1994 | Salo et al. | |
| 5,682,901 A | 11/1997 | Kamen | |
| 5,700,283 A | 12/1997 | Salo | |
| 5,749,367 A * | 5/1998 | Gamlyn et al. | 600/509 |

(Continued)

FOREIGN PATENT DOCUMENTS

EP 0920885 6/1999

(Continued)

OTHER PUBLICATIONS

"U.S. Appl. No. 10/001,223, Amendment and Response filed Nov. 18, 2004 to Non-Final Office Action mailed Jun. 18, 2004", 9 pgs.

(Continued)

*Primary Examiner*—George Manuel
*Assistant Examiner*—Robert N Wieland
(74) *Attorney, Agent, or Firm*—Schwegman, Lundberg & Woessner, P.A.

(57) ABSTRACT

A method for operating a cardiac rhythm management device in which a clinical state vector is computed as a combination of a plurality of parameters related to a patient's heart failure status and compared to a previously computed clinical state vector to determine a clinical trajectory indicative of changes in the patient's heart failure status. Such detected changes in status can be used both as a clinical tool to evaluate treatment and to automatically adjust the operation of the device.

20 Claims, 2 Drawing Sheets

U.S. PATENT DOCUMENTS

| | | | |
|---|---|---|---|
| 5,778,882 | A | 7/1998 | Raymond et al. |
| 5,800,471 | A | 9/1998 | Baumann |
| 6,026,320 | A | 2/2000 | Carlson et al. |
| 6,070,100 | A | 5/2000 | Bakels et al. |
| 6,104,949 | A | 8/2000 | Pitts Crick et al. |
| 6,129,744 | A | 10/2000 | Boute |
| 6,190,324 | B1 | 2/2001 | Kieval et al. |
| 6,277,078 | B1 | 8/2001 | Porat et al. |
| 6,336,903 | B1 | 1/2002 | Bardy |
| 6,397,105 | B1 | 5/2002 | Bouhour et al. |
| 6,409,674 | B1 | 6/2002 | Brockway et al. |
| 6,438,407 | B1 * | 8/2002 | Ousdigian et al. ........... 600/510 |
| 6,456,880 | B1 | 9/2002 | Park et al. |
| 6,473,647 | B1 | 10/2002 | Bradley |
| 6,480,733 | B1 | 11/2002 | Turcott |
| 6,575,912 | B1 | 6/2003 | Turcott |
| 6,645,153 | B2 | 11/2003 | Kroll et al. |
| 6,668,188 | B2 | 12/2003 | Sun et al. |
| 6,668,194 | B2 | 12/2003 | VanHout |
| 6,741,885 | B1 | 5/2004 | Park et al. |
| 6,980,851 | B2 | 12/2005 | Zhu et al. |
| 2001/0034540 | A1 * | 10/2001 | Molin .......................... 607/20 |
| 2001/0037067 | A1 | 11/2001 | Tchou et al. |
| 2002/0087091 | A1 * | 7/2002 | Koyrakh et al. ............. 600/521 |
| 2003/0004548 | A1 | 1/2003 | Warkentin |
| 2003/0083582 | A1 | 5/2003 | Hirsh |
| 2004/0193066 | A1 * | 9/2004 | Carlson et al. .............. 600/509 |
| 2005/0033368 | A1 * | 2/2005 | Fishler et al. .................. 607/9 |
| 2005/0240237 | A1 * | 10/2005 | Zhu et al. ..................... 607/28 |
| 2007/0021979 | A1 * | 1/2007 | Cosentino et al. .............. 705/2 |
| 2007/0083241 | A1 * | 4/2007 | Bardy .......................... 607/3 |
| 2007/0232936 | A1 * | 10/2007 | Mann et al. ................. 600/486 |

FOREIGN PATENT DOCUMENTS

| | | |
|---|---|---|
| EP | 1118307 | 7/2001 |
| WO | WO-03/041797 A2 | 5/2003 |
| WO | WO-03/043691 | 5/2003 |

OTHER PUBLICATIONS

"U.S. Appl. No. 10/001,223, Amendment and Response filed May 9, 2005 to Non-Final Office Action mailed Feb. 9, 2005", 10 pgs.

"U.S. Appl. No. 10/001,223, Non-Final Office Action mailed Feb. 9, 2005", 19 pgs.

"U.S. Appl. No. 10/001,223, Non-Final Office Action mailed Jun. 18, 2004", 15 pgs.

"U.S. Appl. No. 10/001,223, Notice of Allowance mailed Aug. 10, 2005", 6 pgs.

"European Patent Application No. 027939495, Communication mailed Jun. 5, 2008", 11 pgs.

"International Application No. PCT/US02/36821, International Search Report mailed Aug. 11, 2003", 5 pgs.

* cited by examiner

METHOD AND APPARATUS FOR DETERMINING CHANGES IN HEART FAILURE STATUS

CROSS-REFERENCE TO RELATED APPLICATION

This application is a continuation of U.S. patent application Ser. No. 10/001,223, filed on Nov. 15, 2001, now issued as U.S. Pat. No. 6,980,851, the specification of which is incorporated herein by reference.

FIELD OF THE INVENTION

This invention pertains to methods and apparatus for cardiac rhythm management. In particular, the invention relates to cardiac rhythm management devices used to treat heart failure.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. Conventional pacemakers are implanted subcutaneously or submuscularly in a patient's chest and have leads threaded intravenously into the heart to connect the device to electrodes used for sensing and pacing. A programmable electronic controller causes the pacing pulses to be output in response to lapsed time intervals and sensed intrinsic electrical activity (i.e., heart beats not as a result of a pacing pulse). The most common condition for which pacemakers are used is in the treatment of bradycardia, where the ventricular rate is too slow. Atrio-ventricular conduction defects (i.e., AV block) that are permanent or intermittent and sinus node dysfunction represent the most common causes of bradycardia for which permanent pacing may be indicated. If functioning properly, the pacemaker makes up for the heart's inability to pace itself at an appropriate rhythm in order to meet metabolic demand by enforcing a minimum heart rate.

Pacing therapy can also be used in the treatment of heart failure, which refers to a condition where an abnormality of cardiac function causes cardiac output to fall below a level adequate to meet metabolic demand. Cardiac failure can be due to a variety of etiologies with that due to ischemic heart disease being the most common where a diminished coronary blood flow decreases the contractility of the myocardium. Some heart failure patients suffer from some degree of AV block or are chronotropically deficient such that their cardiac function can be improved with conventional bradycardia pacing. It has also been shown, however, that some heart failure patients suffer from intraventricular and/or interventricular conduction defects (e.g., bundle branch blocks) such that their cardiac outputs can be increased by improving the synchronization of right and left ventricular contractions with electrical stimulation. Other conduction defects can occur in the atria. Cardiac rhythm management devices have therefore been developed which provide pacing stimulation to both atria or to both ventricles in an attempt to improve the coordination of cardiac contractions, termed cardiac resynchronization therapy.

SUMMARY OF THE INVENTION

As explained below, chronic heart failure is generally a progressive condition in which various therapeutic measures, including cardiac resynchronization therapy, are employed in order to stabilize the patient and improve symptoms. Progression of the underlying cardiac disease or other stressors, however, can trigger a cascade of events that lead to rapid deterioration of the patient's condition. Heart failure patients are thus routinely followed by clinical visits to ascertain any changes in their heart failure status so that any necessary intervention can be performed as early as possible. Cardiac resynchronization devices, by virtue of their sensing and processing capabilities, present an opportunity to monitor the heart failure status of patients continuously. Sensing data from the sensing channels can be used to derive parameters reflective of the temporal course of cardiac depolarizations that can indicate conduction abnormalities as well as the extent of cardiac dilation. Parameters related to heart failure status can also be clinical data input to the device or derived from various physiological variables sensed by devices having additional functionality. By combining a number of such parameters related to heart failure status, a clinical state vector can be computed that represents an estimate of the patient's current heart failure status. The difference between a presently computed state vector and a previously computed state vector thus represents a clinical trajectory that indicates if and to what degree a patient's heart failure status has changed. The clinical trajectory may also be used to predict how the patient's condition may change in the future.

In one embodiment, a cardiac rhythm management device is programmed to use the computed clinical trajectory to automatically adjust pacing parameters and/or pacing configuration. In another embodiment, the clinical trajectory may be used by a clinician for more general treatment adjustment, with an external communications device such as an external programmer used to communicate with the implanted device. The computation of the clinical trajectory can then be performed by the either the implanted device or the external device.

DETAILED DESCRIPTION

Figure 1:
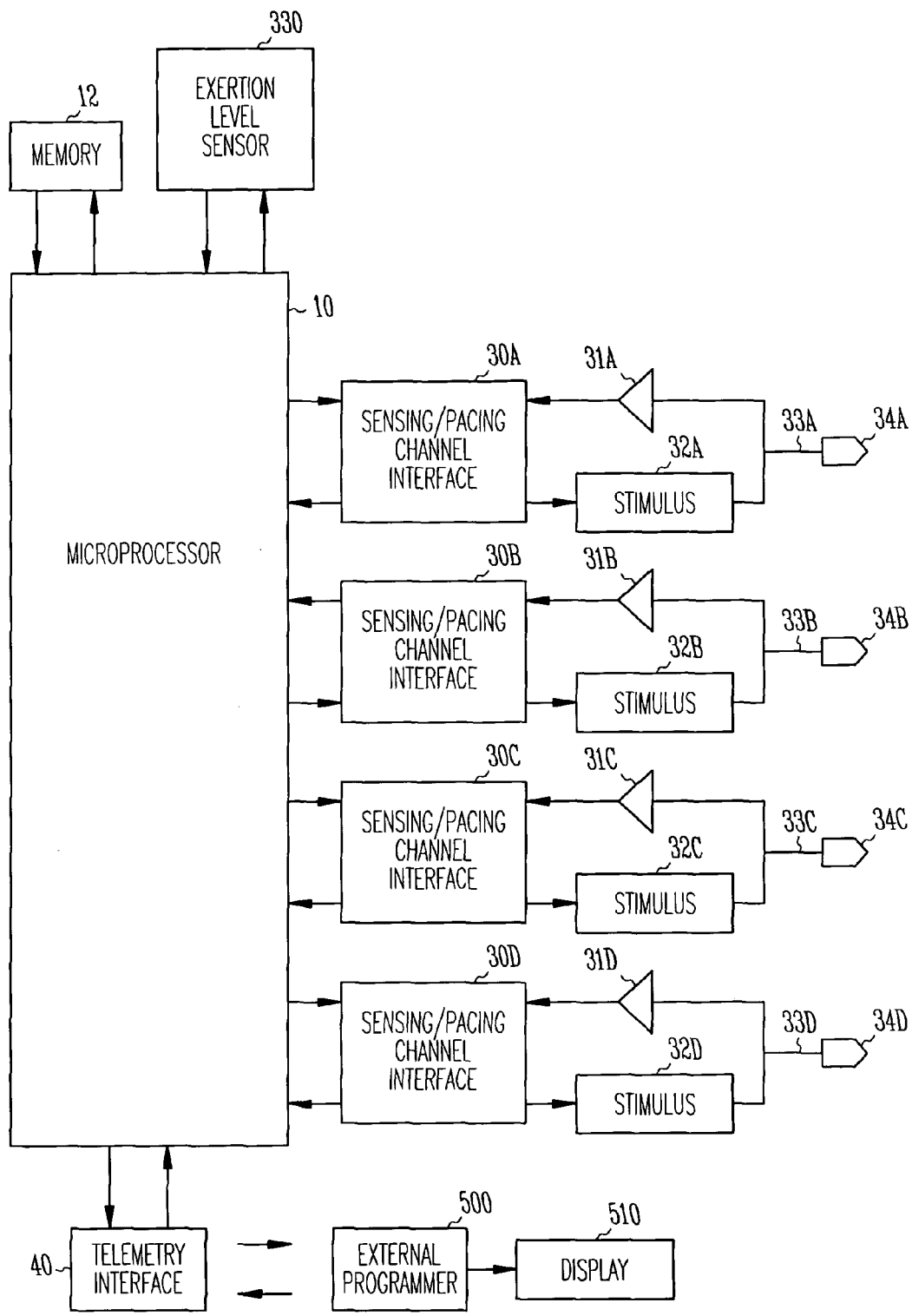
FIG. 1 is a system diagram of a cardiac rhythm management device configurable for resynchronization pacing.

Cardiac failure refers to a condition in which the heart fails to pump enough blood to satisfy the needs of the body. It is usually due to some damage to the heart itself, such as from a myocardial infarction or heart attack. When heart failure occurs acutely, autonomic circulatory reflexes are activated that both increase the contractility of the heart and constrict the vasculature as the body tries to defend against the drop in blood pressure. Venous constriction, along with the reduction in the heart's ability to pump blood out of the venous and pulmonary systems (so-called backward failure), causes an increase in the diastolic filling pressure of the ventricles. This increase in preload (i.e., the degree to which the ventricles are stretched by the volume of blood in the ventricles at the end of diastole) causes an increase in stroke volume during systole, a phenomena known as the Frank-Starling principle. If the heart failure is not too severe, this compensation is enough to sustain the patient at a reduced activity level. When moderate heart failure persists, other compensatory mechanisms come into play that characterize the chronic stage of heart failure. The most important of these is the depressing effect of a low cardiac output on renal function. The increased fluid retention by the kidneys then results in an increased blood volume and further increased venous return to the heart. A state of compensated heart failure results when the factors that cause increased diastolic filling pressure are able to maintain cardiac output at a normal level even while the pumping ability of the heart is compromised.

Compensated heart failure, however, is a precarious state. If cardiac function worsens or increased cardiac output is required due to increased activity or illness, the compensation may not be able to maintain cardiac output at a level sufficient to maintain normal renal function. Fluid then continues to be retained, causing the progressive peripheral and pulmonary edema that characterizes overt congestive heart failure. Diastolic filling pressure becomes further elevated which causes the heart to become so dilated and edematous that its pumping function deteriorates even more. This condition, in which the heart failure continues to worsen, is decompensated heart failure. It can be detected clinically, principally from the resulting pulmonary congestion and dyspnea, and all clinicians know that it can lead to rapid death unless appropriate therapy is instituted.

Resynchronization pacing is effective in treating heart failure because pump function is improved when the ventricles are caused to contract in a more coordinated manner. Heart failure can also be treated medically with diuretics to decrease fluid retention, vasodilators to decrease preload and afterload, and ionotropic agents to increase myocardial contractility. All of these treatment modalities need to be optimized for the individual patient, and therapy adjustments need to be made when a patient's heart failure status changes if the progressive heart failure described above is to be avoided. The present invention includes a method for objectively estimating a patient's heart failure status by computing a clinical state vector as a combination of parameters related to heart failure status. Such parameters may be clinical data, measured physiological variables, or parameters derived therefrom. The clinical state vector may then be compared with a previously computed clinical state vector to determine if the patient's heart failure status has changed.

As described below, the sensing and processing capabilities of a cardiac resynchronization pacemaker can be used to compute a clinical state vector and determine changes in a patient's heart failure status. Not only does this provide a useful diagnostic tool to the clinician for monitoring the effects of treatment, but the pacemaker can also be programmed to automatically adjust its operation when such changes are detected.

1. Device Description

FIG. 1 shows a system diagram of a microprocessor-based cardiac rhythm management device for treating heart failure patients. The device is a pacemaker with multiple sensing and pacing channels configurable for delivering resynchronization pacing to the atria and/or the ventricles. The controller 10 of the device is a microprocessor that communicates with a memory 12 via a bidirectional data bus. The memory 12 typically comprises a ROM (read-only memory) for program storage and a RAM (random-access memory) for data storage. The illustrated device has four sensing and pacing channels comprising electrodes 34A-D for disposition near the heart chamber to be sensed and/or paced, leads 33A-D, sensing amplifiers 31A-D, pulse generators 32A-D, and channel interfaces 30A-D which communicate bidirectionally with microprocessor 10, where the letters a through d designate the individual channels. Each channel may be configured so as to pace and/or sense either a ventricular or atrial site so as to deliver biventricular or biatrial pacing or deliver multi-site pacing to a single chamber. Other embodiments may have more or fewer sensing/pacing channels. In this embodiment, a single electrode is used for sensing and pacing in each channel, known as a unipolar lead. Other embodiments may employ bipolar leads that include two electrodes for outputting a pacing pulse and/or sensing intrinsic activity. In the event that a sensing channel is to be dedicated for use in sensing electrograms, however, a unipolar lead is preferred. The channel interfaces 30A-D include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. An exertion level sensor 330 such as a minute ventilation sensor enables the controller to adapt the pacing rate in accordance with changes in the patient's physical activity. The minute ventilation sensor is a sensor that measures thoracic impedance and can also provide data indicative of cardiac status as explained below. A telemetry interface 40 is provided for communicating with an external programmer 500 that has an associated display 510.

The controller 10 controls the overall operation of the device in accordance with programmed instructions stored in memory. The controller 10 interprets sense signals from the sensing channels and controls the delivery of paces in accordance with a pacing mode. A depolarization wave associated with an intrinsic contraction of the atria or ventricles that is detected by the pacemaker is referred to as an atrial sense or ventricular sense, respectively. The sensing circuitry of the pacemaker generates atrial and ventricular sense signals when voltages sensed by the electrodes exceed a specified threshold. The sense signals from a channel can also be digitized into an electrogram that can be stored in the controller's memory and later transmitted via the telemetry link to an external programmer. In order to cause contraction of a heart chamber in the absence of an intrinsic beat, a pacing pulse (either an atrial pace or a ventricular pace) with energy above a certain pacing threshold is delivered to the chamber. Numerous pacing modes have been developed that specify the manner in which such pacing pulses are delivered and which are useful in the treatment of heart failure, including bradycardia, resynchronization, and anti-tachycardia pacing modes.

Bradycardia pacing modes refer to pacing algorithms used to pace the atria and/or ventricles in a manner that enforces a certain minimum heart rate. As noted earlier, some heart failure patients benefit from bradycardia pacing alone. Also, as explained below, it is advantageous to deliver resynchronization pacing in conjunction with a bradycardia pacing mode. Bradycardia modes are generally designated by a letter code of three positions where each letter in the code refers to a specific function of the pacemaker. Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking pacemakers (i.e., VDD or DDD mode), another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing attempts to maintain the atrio-ventricular synchrony occurring with physiological beats whereby atrial contractions augment diastolic filling of the ventricles. If a patient has a physiologically normal atrial rhythm, atrial-tracking pacing also allows the ventricular pacing rate to be responsive to the metabolic needs of the body.

A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing (i.e., DDD mode), the lower rate limit interval is then the sum of the atrial escape interval and the atrio-ventricular interval.

Rate-adaptation may also be used in bradycardia pacing modes. In rate-adaptive pacing, the ventricular and/or atrial escape intervals are modulated based upon measurements corresponding to measured exertion levels. In a rate-adaptive pacemaker operating in a ventricular pacing mode, the LRL is adjusted in accordance with exertion level measurements such as from an accelerometer or minute ventilation sensor in order for the heart rate to more nearly match metabolic demand. A given exertion level is mapped to a particular LRL, termed the sensor-indicated rate, by a rate response curve, the slope of which determines the responsiveness of the rate-adaptation. Rate-adaptive pacing is applicable to situations where atrial tracking modes are contraindicated, such as in patients prone to atrial arrhythmias.

Cardiac resynchronization therapy is pacing stimulation applied to one or more heart chambers in a manner that restores or maintains synchronized bilateral contractions of the atria and/or ventricles. Ventricular resynchronization pacing is useful in treating heart failure because, although not directly ionotropic, resynchronization results in a more coordinated contraction of the ventricles with improved pumping efficiency and increased cardiac output. Resynchronization pacing of the atria may also be beneficial in certain heart failure patients, particularly for preventing the onset of atrial arrhythmias. One way to deliver resynchronization therapy is to pace a site with a synchronous bradycardia pacing mode and then deliver one or more resynchronization paces to one or more additional pacing sites in a defined time relation to one or more selected sensing and pacing events that either reset escape intervals or trigger paces in the bradycardia pacing mode. One such resynchronization pacing mode may be termed offset resynchronization pacing. In this mode, a first site is paced with a bradycardia mode, and a second site receives a resynchronization pace at an offset interval with respect to the pace delivered to the first site. The offset interval may be zero in order to pace both sites simultaneously, positive in order to pace the first site after the second, or negative to pace the first site before the second. For example, in biventricular resynchronization pacing, one ventricle is paced with a bradycardia mode while the contralateral ventricle receives resynchronization paces at the specified biventricular offset interval. The offset interval would normally be individually specified to optimize cardiac output in a particular patient. Ventricular resynchronization can also be achieved in certain patients by pacing at a single unconventional site, such as the left ventricle instead of the right ventricle. In such a mode, right ventricular senses may be used to trigger left ventricular paces or used to define an escape interval that upon expiration causes delivery of a left ventricular pace.

Because heart failure patients have a high incidence of sudden death due to the onset of ventricular fibrillation and other arrhythmias, it is advantageous for a cardiac rhythm management device to also have the capability of delivering cardioversion/defibrillation shocks. The device in FIG. 1 thus includes a shock pulse generator 50 interfaced to the microprocessor for delivering cardioversion or defibrillation pulses to the heart via a pair of electrodes 51*a* and 51*b*. The device may also deliver paces in accordance with an anti-tachycardia pacing (ATP) protocol in order to treat certain arrhythmias. In ATP, the heart is competitively paced with one or more pacing pulses in an effort to interrupt reentrant circuits causing the tachycardia. Generally, only cardioversion/defibrillation will terminate fibrillation and certain high rate tachycardias, while ATP can be used to treat lower rate tachycardias. ATP therapy may thus be initiated when a tachycardia is detected, while a shock pulse is delivered when fibrillation occurs.

One or more of the sensing channels of the device are used to detect arrhythmias. Ventricular fibrillation (VF) may be distinguished from ventricular tachycardia (VT) using rate-based criteria so that ATP or shock therapy can be delivered as appropriate. The heart rate is usually measured by detection of the time between successive ventricular senses. A measured heart rate is classified as a tachycardia when the rate is in a VT zone, defined as a range of rates above a tachycardia detection rate (TDR) but below a fibrillation detection rate (FDR). A measured heart rate above the FDR, on the other hand, is in the VF zone and is classified as a fibrillation. A tachycardia with a heart rate in the VT zone may then be treated with ATP therapy in order to avoid an unnecessary painful shock to the patient, while a defibrillation shock is delivered if the pacing fails to terminate the arrhythmia.

2. Computation of Clinical Trajectory

In order to estimate a patient's heart failure status, a clinical state vector can be computed from a combination of measured or derived parameters that have some to relation to an aspect of heart failure such that changes in a parameter's value correlates with worsening or improvement in the patient's condition. Such a state vector thus represents a composite estimation of the patient's heart failure status where each parameter is given a specified weighting according to its clinical significance. By comparing the present clinical state vector with a previously computed state vector, a clinical trajectory may be computed that indicates if and to what extent the patient's condition has changed and/or how the patient's condition may continue to change. The clinical trajectory is a vector quantity that indicates the magnitude and direction of the change in the clinical state vector. An objective determination of the patient's clinical trajectory in this manner allows a clinician to detect possible progression toward decompensation earlier than waiting until clinical signs or symptoms of worsening heart failure become apparent. Appropriate therapy adjustments can then be made to reverse or stabilize the process in a more timely and effective manner. The clinical trajectory can also be used to provide diagnostic information to a physician when a new therapy (e.g., either a device-based therapy or a drug) is prescribed.

In a particular embodiment, the processor of an implantable cardiac rhythm management device such as a cardiac resynchronization pacemaker is programmed to compute a clinical trajectory and determine changes in heart failure status as described above. One or more of the clinical parameters are derived from sense signals generated by either one of the device's sensing channels or by other types of sensors that may be incorporated into the device such those for measuring exertion level and blood pressures. Clinical parameters obtained by other means may be input to the implantable device's processor from an external programmer during a communications session via the telemetry link. Some of the processing for computation of the clinical trajectory may also be performed by the external programmer during such a communications session. Detected changes in heart failure status may then be communicated to a clinician for treatment decisions and/or used by the device to automatically adjust its pacing operation.

The device may be programmed to automatically adjust its operation in accordance with the scheme when the magnitude of a computed clinical trajectory and/or a clinical state vector exceeds a specified limit value. The automatic adjustment of pacing operation may be performed according to a predetermined scheme in which a particular clinical trajectory or state vector is mapped to a particular set of pacing parameters and/or pacing configuration. The pacing configuration specifies the pacing mode and which of the sensing/pacing channels available to the device are to be used. When the computed clinical trajectory or state vector reaches a specified limit value, the device may be programmed to change the pacing configuration by switching the pacing channel or channels and/or changing the pacing mode. For example, resynchronization pacing of the atrial and/or ventricles may only be employed when the patient's heart failure worsens to a certain point as measured by the computed clinical trajectory or state vector. Among the pacing parameters that may also be adjusted in accordance with the computed clinical trajectory or state vector once a pacing configuration is selected are the ventricular escape interval or LRL for ventricular pacing, the atrial escape interval for atrial pacing, the atrio-ventricular interval for atrial tracking pacing, the offset interval for biventricular or biatrial offset pacing, the slope of rate-response curve for rate-adaptive pacing, and the maximum pacing rate.

As aforesaid, certain of the clinical parameters used to compute the clinical trajectory may be derived from the sense signals of the implantable device's sensing channels such as QRS duration, interventricular delay between left and right ventricular senses, heart rate variability, and PR interval. Such parameters reflect the temporal course of depolarization activity during a cardiac cycle and may provide an indication of the patient's cardiac conduction status and/or the extent of cardiac dilation. Other parameters derived from sense signals may relate to the frequency of certain events occurring over a specified period of time including the frequency of atrial fibrillation, conversion of ventricular tachycardia to ventricular fibrillation (VT/VF occurrence), or frequency of ectopic beats. The device may also be configured to measure or derive other parameters including body temperature during exercise, changes in activity levels, an average of the patient's exertion level over a specified period of time, and changes in the ratio of minute ventilation to activity level as a measure of functional capacity. If the device has a thoracic impedance sensor for measuring minute ventilation, a parameter related to the frequency of decompensation events may be obtained by detecting pulmonary congestion. Other parameters not measured by the device itself and incorporated into the clinical trajectory including a direct or derived left ventricular end diastolic pressure, systolic pressure index, pulse pressure index, maximum rate of change in left ventricular pressure rise dP/dt, and body weight.

A clinical state vector may be defined as a mapping of each clinical parameter to an ordinal scale that represents a coordinate axis in an n-dimensional vector space, where n is the total number of parameters. The total clinical state vector is then a point in the vector space that reflects the patient's overall clinical condition relating to heart failure. By adjusting the ordinal scale used to map individual parameter to coordinates in the vector space, a weighting is may be effectively assigned to each parameter based upon its clinical significance. For example, a weighting factor $a_i$ may be assigned to each parameter $X_i$ based upon its clinical significance to form an n-dimensional clinical state vector that is a function of a plurality of clinical parameters. A clinical trajectory index CT, representing a magnitude of a clinical state vector, can then be computed as a sum of the weighted parameters:

$$CT=\Sigma a_i X_i$$

where the summation is carried out from i=1 to N and N represents the total number of parameters. The clinical trajectory index CT can be compared with specified threshold values to estimate heart failure status.

Over the time course when the patient's condition changes as a result of receiving different therapies or otherwise, the clinical state vector changes accordingly and may be mapped and recorded for physician and/or device use. Computing the changes in the clinical state vector results in a clinical trajectory that indicates how the patient's condition is changing. For example, computing the vector difference between a present and a past clinical state vector results in a clinical trajectory with both a magnitude and direction in the n-dimensional vector space. The magnitude of the clinical trajectory, either computed directly or represented by the clinical trajectory index, then indicates how much the patient's condition has changed. The direction of the change in the vector space indicates whether the changes in the patient's clinical parameters represent a worsening or improvement in clinical status.

Figure 2:
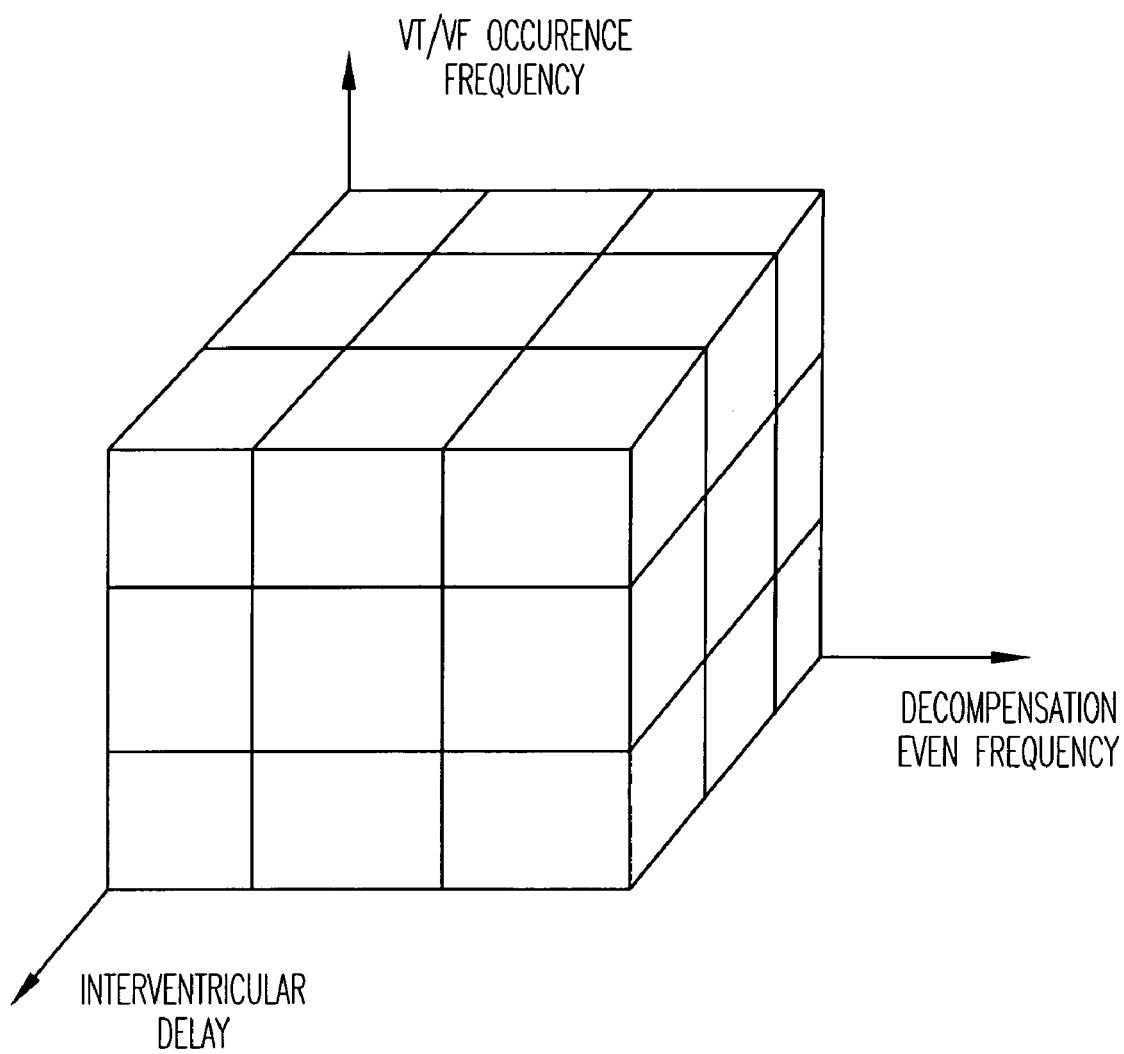
FIG. 2 illustrates an exemplary implementation of a clinical vector space.

An exemplary implementation is illustrated in FIG. 2 where a three-dimensional clinical state vector is formed from three clinical parameters: frequency of decompensation events, frequency of VT/VF occurrence, change of interventricular delay as an indication of ventricular dilation. The decompensation event frequency and VT/VF frequency are each mapped to a three-value ordinal scale as either low, medium, or high. The change in interventricular delay is mapped to a three-value ordinal scale as either small, medium, or large. As shown in FIG. 2, the clinical state vector may have one of eighteen possible values at any given time in the vector space based upon the values of each parameter. The particular values of a parameter that are mapped to particular coordinate values thus represent a weighting of the parameter. The parameters may be mapped such that the magnitude of the clinical state vector (i.e., its distance from the origin) gives an estimate of the patient's clinical condition related to heart failure. The clinical trajectory may then be computed as the vector difference between a present and a past clinical state vector, with the direction of the trajectory indicating whether the patient is worsening or improving and the magnitude of the trajectory indicating the extent of change. Any of the clinical parameters enumerated above could be used in the same way to form a clinical state vector. Also, although this example has used only three clinical parameters, it should be appreciated that the same concept can be generalized to any number of clinical parameters that form an n-dimensional clinical vector space.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A system, comprising:
    an implantable device having one or more sensing modalities and pacing circuitry for delivering pacing therapy;
    an external programmer for the implantable device;
    a telemetry interface enabling communication between the external programmer and the implantable device;
    wherein the external programmer is programmed to compute a clinical state vector as a combination of a plurality of parameters related to a patient's heart failure status, wherein the plurality of parameters define an n-dimensional vector space with n being the number of parameters and with each parameter mapped to an ordinal scale that represents a coordinate axis in the n-dimensional vector space, and further wherein the n parameters include at least one parameter derived from data transmitted by the implantable device;
    wherein the external programmer is further programmed to compute a difference vector between the computed clinical state vector and a previously computed state vector, wherein the magnitude of the difference vector indicates the extent of change in the patient's heart failure status and the direction of the difference vector indicates whether the patient's heart failure status is improving or worsening; and,
    wherein the implantable device is programmed to change a pacing configuration for delivering pacing therapy if the computed difference vector exceeds a specified limit value.

2. The system of claim 1 wherein the at least one parameter derived from data transmitted by the implantable device corresponds to a PR interval in an electrogram.

3. The system of claim 1 wherein the at least one parameter derived from data transmitted by the implantable device corresponds to a QRS duration in an electrogram.

4. The system of claim 1 wherein the at least one parameter derived from data transmitted by the implantable device corresponds to an inter-ventricular delay between senses in the right and left ventricles.

5. The system of claim 1 wherein the plurality of parameters includes a frequency of atrial fibrillation occurrence over a specified period of time.

6. The system of claim 1 wherein the plurality of parameters includes a frequency at which a ventricular tachycardia converts to ventricular fibrillation over a specified period of time.

7. The system of claim 1 wherein the plurality of parameters includes a measure of heart rate variability.

8. The system of claim 1 wherein the plurality of parameters includes a measured body weight of the patient.

9. The system of claim 1 wherein the plurality of parameters includes a measured or derived left ventricular end diastolic pressure.

10. The system of claim 1 wherein the plurality of parameters includes a measured or derived systolic pressure index.

11. The system of claim 1 wherein the plurality of parameters includes a measured or derived pulse pressure index.

12. The system of claim 1 wherein the plurality of parameters includes a measured or derived maximum left ventricular dP/dt index.

13. The system of claim 1 wherein the plurality of parameters includes a frequency of ectopic beats over a specified period of time.

14. The system of claim 1 wherein the plurality of parameters includes a ratio of minute ventilation to activity level.

15. The system of claim 1 wherein the external programmer is further programmed to compute a clinical trajectory index CT computed as a sum of the weighted parameters:

$$CT = \Sigma a_i X_i$$

where a weighting factor $a_i$ is assigned to each parameter $X_i$ based upon its clinical significance and the summation is carried out from i=1 to N, N representing the total number of parameters.

16. An external programmer for an implantable medical device, comprising:
    means for computing a clinical state vector as a combination of a plurality of parameters related to a patient's heart failure status, wherein the plurality of parameters define an n-dimensional vector space with n being the number of parameters and with each parameter mapped to an ordinal scale that represents a coordinate axis in the n-dimensional vector space, and further wherein the n parameters include at least one parameter derived from data transmitted by the implantable device;
    means for computing a difference vector between the computed clinical state vector and a previously computed state vector, wherein the magnitude of the difference vector indicates the extent of change in the patient's heart failure status and the direction of the difference vector indicates whether the patient's heart failure status is improving or worsening; and,
    means for communicating with the implantable device to cause the implantable device to change a pacing configuration for delivering pacing therapy if the computed difference vector exceeds a specified limit value.

17. The external programmer of claim 16 wherein the plurality of parameters includes a measured or derived left ventricular end diastolic pressure.

18. The external programmer of claim 16 wherein the plurality of parameters includes a measured or derived systolic pressure index.

19. The external programmer of claim 16 wherein the plurality of parameters includes a measured or derived pulse pressure index.

20. The external programmer of claim 16 wherein the plurality of parameters includes a measured or derived maximum left ventricular dP/dt index.

* * * * *